United States Patent [19]

Smith

[11] Patent Number: 4,800,225

[45] Date of Patent: Jan. 24, 1989

[54] PHARMACOLOGICALLY ACTIVE HYDRATED AZABICYCLO COMPOUND

[75] Inventor: Paul Smith, Harlow, England

[73] Assignee: Beecham Group, p.l.c., Brentford, England

[21] Appl. No.: 28,256

[22] Filed: Mar. 20, 1987

[30] Foreign Application Priority Data

Mar. 22, 1986 [GB] United Kingdom ............... 8607163

[51] Int. Cl.$^4$ ........................................... C07D 471/08
[52] U.S. Cl. ................................................... 546/112
[58] Field of Search ....................................... 546/112

[56] References Cited

U.S. PATENT DOCUMENTS 4,612,319 9/1986 King ................................... 546/112

FOREIGN PATENT DOCUMENTS 94742 11/1983 European Pat. Off. .

OTHER PUBLICATIONS

Berge et al., J. of Pharmaceutical Sciences, 66(1), pp. 1-3.
Lackman et al., The Theory and Practice of Industrial Pharmacy, 2nd. Ed. (Lea and Febiger, Philadelphia), pp. 99-107 (1976).
Shefter et al., J. of Pharmaceutical Sciences, 52(8), pp. 781-791 (1963).

*Primary Examiner*—Mary C. Lee
*Assistant Examiner*—Bernard I. Dentz
*Attorney, Agent, or Firm*—James F. Haley, Jr.; David K. Barr

[57] ABSTRACT

A pure, crystalline hydrate of (±)endo-4-amino-5-chloro-2-methoxy-N-(1'-azabicyclo[3.3.1]non-4'-yl)-benzamide hydrochloride, having useful pharmacological activity namely gastric motility enhancing activity, anti-emetic activity and 5-HT M-receptor antagonist activity.

6 Claims, No Drawings

PHARMACOLOGICALLY ACTIVE HYDRATED AZABICYCLO COMPOUND

This invention relates to the hydrochloride salt of a benzamide in a novel form, and having pharmacological activity, to a process for its preparation and to its use as a pharmaceutical.

EP-A-94742 discloses a class of substituted azabicyclo compounds which are described as having dopamine antagonist activity, useful in the treatment of disorders relating to impaired gastro-intestinal motility, such as retarded gastric emptying, dyspepsia, flatulence, oesphageal reflux and peptic ulcer. Depending on their balance between peripheral and central action on the nervous system, they may also be used in the treatment of emesis and/or the treatment of disorders of the central nervous system, such as psychosis. Compound No. 6 (described under Example 9) is($\pm$)4-amino-5-chloro-2-methoxy-N-(4'[1'-azabicyclo(3,3,1)-nonyl])-benzamide, the endo isomer of which is hereinafter referred to as 'Compound 1'.

The hydrochloride salt of Compound 1 is preferred over the free base because of its improved solubility.

It is important, however, that the solid product should be stable and have good handling qualities for commercial production.

A pure, crystalline hydrate of the hydrochloride salt of Compound 1 has now been discovered, this hydrate having useful pharmacological activity, namely gastric motility enhancing activity, anti-emetic activity and 5-HT M-receptor antagonist activity.

This hydrate exists in crystalline form, and has improved handling and stability characteristics over the anhydrous hydrochloride salt of Compound 1.

Accordingly, the present invention provides a hydrochloride salt hydrate of Compound 1.

The hydrate contains 5-15% water by weight, often between 10 and 12.5% water.

The hydrate is preferably in pharmaceutically acceptable form. By pharmaceutically acceptable form is meant, inter alia, of a pharmaceutically acceptable level of purity excluding normal pharmaceutical additives such as diluents and carriers, and including no material considered toxic at normal dosage levels. A pharmaceutically acceptable level of purity will generally be at least 50% excluding normal pharmaceutical additives, preferably 75%, more preferably 90% and still more preferably 95%. One preferred pharmaceutically acceptable form is the crystalline form, including such form in a pharmaceutical composition.

The invention also provides a process for the preparation of a hydrate of the hydrochloride salt of Compound 1 which process comprises hydrating the hydrochloride salt of Compound 1 by exposing it to water vapour.

The hydrochloride salt may be placed in a tray over water in a closed vessel at 0° to 50° C., usually at ambient temperature. The exposure time is preferably greater than 24 hours, usually about 36 hours.

When large quantities of material are to be prepared, it may be preferable to introduce a method of agitation to the hydrochloride salt in oroer to facilitate water absorption.

The hydrochloride salt is formed conventionally. Compound 1 as the free base (prepared as described in EP-A-94742) is dissolved in a suitable solvent, preferably ethanol, and a solution of hydrogen chloride in a suitable solvent, preferably ethanol, is added, allowing the product to precipitate.

The salt produced may be solvated to a certain extent (e.g. containing ethanol). When this product is hydrated as hereinbefore described, organic solvents, such as ethanol and ether, which may already partially solvate the hydrochloride salt, are removed, thus avoiding any problems which may be associated with organic solvent incorporation into a drug to be used for administration to mammals, including humans.

The compound of the present invention has gastric motility enchancing, anti-emetic and 5-HT antagonist activity. Compounds having gastric motility enhancing activity are useful in the treatment of disorders such as retarded gastric emptying, dyspepsia, flatulence, oesophageal reflux and peptic ulcer. Compounds having 5-HT antagonist activity are useful in the treatment of migraine, cluster headaches, trigeminal neuralgia and/or cytotoxic agent or radiation induced nausea and vomiting. Examples of cytotoxic agents include cisplatin, adriamycin and cyclophosphamide.

The invention also provides a pharmaceutical composition comprising the hydrochloride salt hydrate of Compound 1, and a pharmaceutically acceptable carrier.

Such compositions are prepared by admixture and are suitably adapted for oral or parenteral administration, and as such may be in the form of tablets, capsules, oral liquid preparations, powders, granules, lozenges, reconstitutable powers, injectable and infusable solutions or suspensions or suppositories. Orally administrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to wel known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

The oral compositions may be prepared oy conventional methods of blending, filling or tabletting. Repeated blending operations may be used to distribute the active agent throughout those compositions employing large quantities of fillers. Such oerations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance tne stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound of the invention.

The invention further provides a method of treatment or prophylaxis of disorders relating to impaired gastro-intestinal motility and/or emesis and/or migraine, cluster headache, trigeminal neuralgia emesis in mammals, such as humans, which comprises the administration of the hydrochloride salt hydrate of Compound 1.

An amount effective to treat the disorders hereinbefore described depends on the relative efficacies of the compounds of tne invention, the nature and severity of the disorder being treated and the weight of the mammal. However, a unit dose for a 70 kg adult will normally contain 0.5 to 1000 mg for example 1 to 500 mg, of the compound of the invention. Unit doses may be administered once or more than once a day, for example, 2, 3 or 4 times a day, more usually 1 to 3 times a day, that is in the range of approximately 0.001 to 50 mg/kg/day, more usually 0.002 to 25 mg/kg/day.

No adverse toxicological effects are indicated at any of the aforementioned dosage ranges.

No adverse toxicological effects are indicated at any of the aforementioned dosage range.

The invention also provides the hydrochloride salt hydrate of Compound 1 for use as an active therapeutic substance, in particular for use in the treatment of disorders relating to impaired gastro-intestinal motility and/or emesis and/or migraine, cluster headache, trigeminal neuralgia.

The following Example illustrates the invention.

EXAMPLE ($\pm$-endo)-4-Amino-5-chloro-2-methoxy-N-1'-azabicyclo[3.3.1]non-4'-yl)-benzamide hydrochloride hydrate.

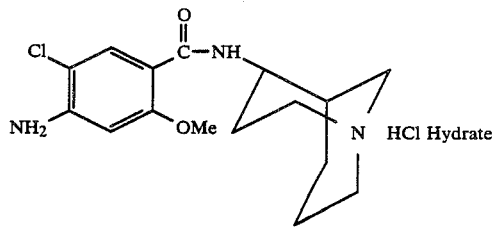

(i) preparation of hydrochloride salt

The free base of Compound 1 (1273 g) was heated in ethanol (6.01) to reflux and filtered through celite which was washed with ethanol (250 ml). Ethanolic hydrogen chloride solution (830 ml, 4.74M) was added to the filtrate causing the product to precipitate. The product was allowed to cool to 25° C. in an ice/water bath for 1 hour and then collected by filtration, washed with ethanol (1.01) and dried in a vacuum oven at 60° C. for 8 hours. Yield:1300 g (contained 2.5% ethanol).

(ii) Preparation of hydrate

The material prepared in (i) was placed on a tray over water in a closed vessel for 36 hours. This removed all traces of ethanol and gave the hydrated product containing 11.4% water. Yield:1397 g m.p. 226°–233° C.

I claim:

1. ($\pm$)endo-4-Amino-5-chloro-2-methoxy-N-(1'-azabicyclo-[3.3.1]non-4'-yl)benzamide, hydrochloride salt hydrate.

2. A compound according to claim 1 wherein the hydrate contains 5–15% water.

3. A compound according to claim 1 wherein the hydrate contains between 10 and 12.5% water.

4. A compound according to claim 1 in pharmaceutically acceptable crystalline form.

5. A pharmaceutical composition for use in the treatment of disorders relating to impaired gastro-intestinal motility, emesis, migraine, cluster headache and/or trigeminal neuralgia comprising an effective amount of a compound according to any one of claims 1 to 4 and a pharmaceutically acceptable carrier.

6. A method of treatment of disorders relating to impaired gastro-intestinal motility, emesis, migraine, cluster headache and/or trigeminal neuralgia which comprises the administration to the mammal of an effective amount of a compound according to claim 1.

* * * * *